United States Patent [19]

Sabee

[11] Patent Number: 4,995,928
[45] Date of Patent: Feb. 26, 1991

[54] METHOD AND APPARATUS FOR FORMING AND TRANSPORTING ELASTIC RIBBONS

[76] Inventor: Reinhardt N. Sabee, 728 S. Summit St., Appleton, Wis. 54911

[21] Appl. No.: 267,303

[22] Filed: Oct. 31, 1988

[51] Int. Cl.⁵ .................... B32B 31/08; B32B 31/30
[52] U.S. Cl. .................... 156/164; 156/229; 156/259; 156/244.11; 156/244.12; 156/244.19; 156/495; 156/517; 156/522; 156/556
[58] Field of Search .............. 156/164, 495, 244.11, 156/161, 229, 494, 522, 244.12, 244.19, 517, 556, 259; 264/229; 425/113, 115, 383, 404; 604/385.2

[56] References Cited

U.S. PATENT DOCUMENTS

| | | | |
|---|---|---|---|
| 3,738,884 | 6/1973 | Soehngen | 156/167 |
| 4,295,919 | 10/1981 | Sutrina et al. | 156/244.11 X |
| 4,428,788 | 1/1984 | Kamp | 156/244.11 X |
| 4,525,229 | 6/1985 | Suzuki et al. | 156/164 X |
| 4,543,099 | 9/1985 | Bunnelle et al. | 156/164 X |
| 4,556,596 | 12/1985 | Meuli | 428/184 X |
| 4,578,133 | 3/1986 | Oshefsky et al. | 156/164 |
| 4,618,384 | 10/1986 | Sabee | 156/205 |
| 4,656,075 | 4/1987 | Mudge | 156/244.11 X |
| 4,666,542 | 5/1987 | De Jonckheere | 156/164 |
| 4,675,016 | 6/1987 | Meuli et al. | 156/164 X |

FOREIGN PATENT DOCUMENTS

59-122570 7/1984 Japan .................. 156/243

Primary Examiner—Michael W. Ball
Assistant Examiner—Michele K. Yoder
Attorney, Agent, or Firm—Fuller, Ryan & Hohenfeldt

[57] ABSTRACT

A carrier strip or filament of cold drawable material is utilized to transport discrete lengths of elastic ribbon within a manufacturing apparatus. The elastic ribbons are extruded onto the carrier strip or around the filament and adhere thereto. The carrier strip and elastic ribbon are jointly stretched a predetermined amount. The stretched carrier strip and stretched elastic ribbon are bonded to a component of a final product, as, for example, the backing sheet of a disposable diaper, wherein the elastic ribbons are employed to elasticize the leg areas. The carrier strips greatly facilitate machine handling relatively short lengths of stretched elastic ribbons without waste. The carrier strips may be transversely guided along a predetermined path to follow the hourglass contour of the margins of a diaper having form fitting legs.

42 Claims, 6 Drawing Sheets

METHOD AND APPARATUS FOR FORMING AND TRANSPORTING ELASTIC RIBBONS

This is a divisional of co-pending application Ser. No. 790,955 filed on Oct. 4, 1985 now U.S. Pat. No. 4,813,946.

BACKGROUND OF THE INVENTION

1. Field of the Invention

This invention pertains to methods and apparatus for applying elastic ribbons to webs of material, and more particularly to methods and apparatus for applying discrete lengths of stretched elastic ribbon to predetermined areas of a continuously moving web.

2. Description of the Prior Art.

The development of adult and infant disposable diapers is summarized in the article "New Trends in Adult Pads and Infant Diapers," by Francis J. Bouda, Non-Woven Industry, January 1983. Modern disposable diapers employ elastic ribbons, especially in the crotch area, to assist in preventing leakage of body discharges around the wearer's legs.

Various equipment has been developed to deal with the problems associated with handling the elastic ribbons applied to the sheets of diaper material. One problem is the holding of discrete lengths of elastic ribbons in the proper location during the manufacturing operation. The use of vacuum systems to hold the pieces to elastic ribbon is well known and is illustrated in U.S. Pat. Nos. 4,360,398; 4,379,016; and 4,397,704. However, vacuum systems are expensive to build and operate, and they do not provide positive retention of the ribbons.

An associated problem concerns the requirement that the elastic ribbon be applied to the moving web of diaper material such that when the ribbons are relaxed they bunch up the diaper to snug the wearer's legs. One solution to this problem is to corrugate the web material and to apply discrete pieces of elastic ribbon in a relaxed state to the peaks of the corrugations, as disclosed in U.S. Pat. Nos. 4,379,016 and 4,397,704. These designs have the advantage of utilizing only as much ribbon material as is necessary. However, the grooved drums required for corrugating the web are costly to manufacture, as is the vacuum system required to retain the web within the drum corrugations.

A second solution is to attach the elastic ribbons when in the stretched condition to the underlying webs. U.S. Pat. Nos. 4,081,301 and 4,360,398 exemplify this approach. The disadvantage is that a portion of elastic ribbon material is wasted because typically the elastic ribbons are applied only to the crotch regions of the diaper. It has been calculated that 50% of elastic material is wasted by this method. That represents a loss of $75,000.00 per year in some instances. The apparatus of U.S. Pat. No. 4,227,952 applies a stretched elastic ribbon to the web in a manner that does not waste ribbon material, but that apparatus is complicated to manufacture and maintain.

U.S. Pat. No. 3,694,815 utilizes a cryogenic bath in which a stretched elastic ribbon is immersed, thereby immobilizing the ribbon for attaching to the garment fabric; upon warming, elastic ribbon acquires its elastic properties.

U.S. Pat. No. 4,284,454 teaches methods and apparatus for mechanically gripping length of elastic ribbon for transverse placement on a continuous fabrication line. It is evident that the equipment of the U.S. Pat. No. 4,284,454 is complicated and costly.

Thus, a need exists for simple and economical apparatus which handles and attaches discrete pieces of elastic ribbon without waste to a continuously moving web.

SUMMARY OF THE INVENTION

In accordance with the present invention, apparatus is provided for forming discrete lengths of elastic ribbon for attachment to an underlying continuously moving web in a more economical and effective manner than was heretofore possible. This is accomplished by supplying a carrier strip or carrier filament and adhering the discrete elastic lengths to the strip. The carrier member affords convenient handling of the elastic during application to the diaper material. The carrier strip can be extruded and the lengths of elastic ribbon bonded to the strip.

Figures 21, 22, 23, 24, 25:
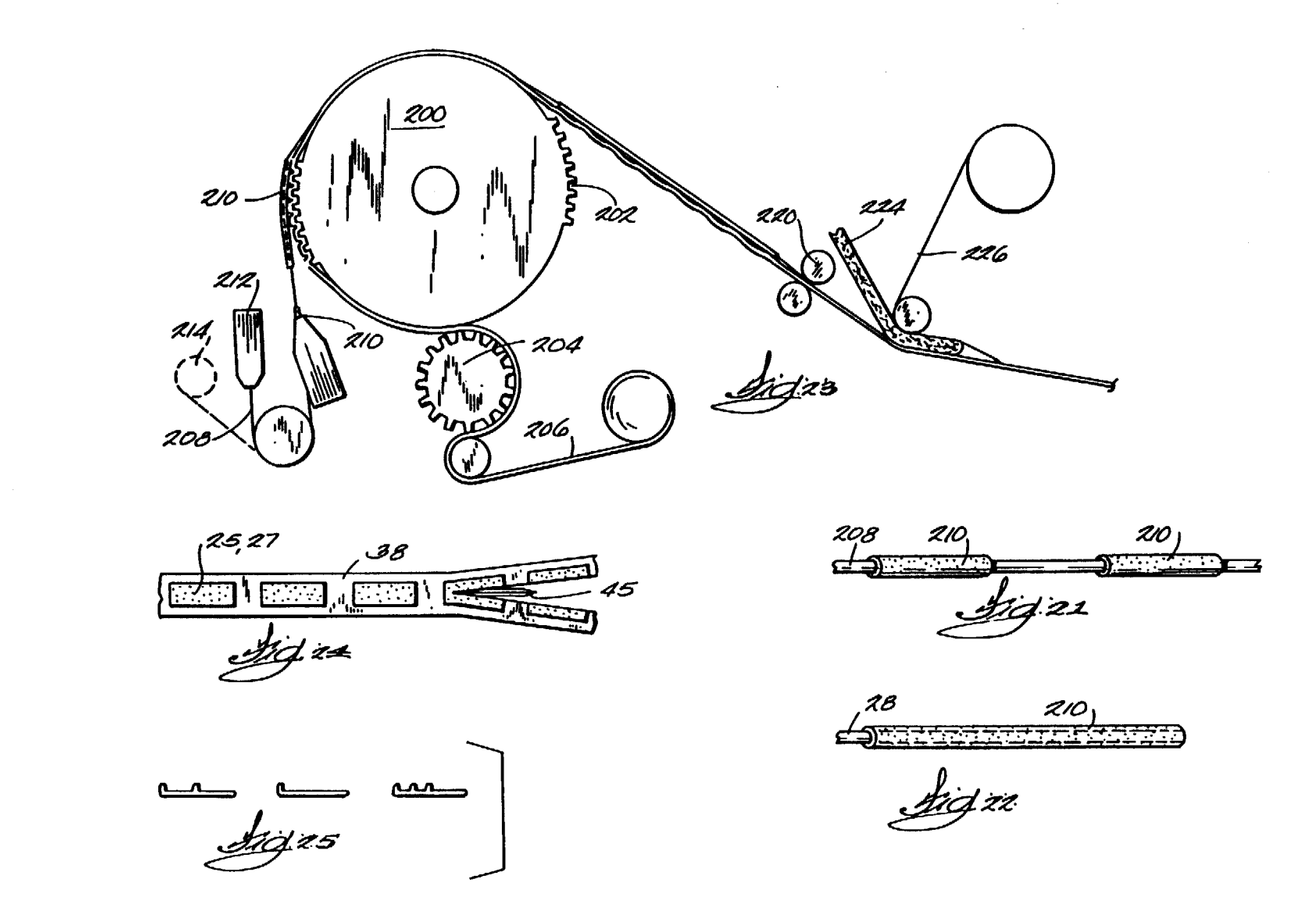
FIG. 21 is a diagrammatic view of a modified embodiment of carrier member in the form of an elastic tube with carrier filament inside.
FIG. 22 is a view similar to FIG. 21 of a further modified embodiment.
FIG. 23 is a diagrammatic view of a further modified method of the invention.
FIG. 24 is a top view of a carrier strip and spaced elastic ribbons.
FIG. 25 shows various cross sections of elastic ribbons.

The carrier strip can be extruded as a continuous stream, preferably from a cold drawable material onto a rotating chill roll. The elastic ribbons may be extruded in place as a pair of transversely spaced streams of molten or heat softened material which are deposited onto the carrier strip. Alternatively, the elastic ribbon material may be extruded onto the carrier strip a short distance downstream from the carrier strip extruding nozzle. The elastic ribbons are not necessarily extruded continuously onto the carrier strip, but rather they may be extruded intermittently into discrete lengths. A cooling air jet or moisture atomizing means, water cooling and other cooling means may be applied to the extruded carrier strip and elastic ribbon. Upon cooling and solidifying, the molten carrier strip and elastic ribbon extrudates acquire at least some cold drawable and elastomeric properties, respectively, and the elastic ribbons thus formed adhere firmly to the carrier strip. The elastic carrier strip assembly can be formed with co-extrusion nozzles with the carrier extruded in the form of a tube with the elastic extruded within the tube. Adhesive can also be extruded within the carrier tube to secure the elastic ribbon to the carrier. Patterned rollers can be employed rather than or in connection with adhesive to press the elastic into an interlocking pattern with the carrier tube. Patterned rollers can produce elastic bands of various shapes such as shown in FIG. 25.

After the carrier strip or tube and elastic ribbons have cooled sufficiently, they are withdrawn from the chill roll for processing into a finished product, such as a disposable diaper. For that purpose, the carrier strip may be longitudinally slit in half as it continuously moves past a knife, with each half carrying an elastic ribbon.

The carrier strips, being of drawable material, together with the elastic ribbons, are then stretched the proper amount for the product being made. The carrier strips and elastic ribbons are spread apart transversely to the approximate width of the underlying web, thereby locating the elastic ribbons near the web margins.

The elastic ribbons are thus conveniently and inexpensively transported by the carrier strips to an assembly station, where they are combined with the remainder of the diaper components while in a stretched condition, such as an absorbent pad, backing sheet, and facing sheet, into a unitary garment. Upon release of the tension in the stretched elastic ribbons, the ribbons relax to pucker the diaper into a form fitting elasticized garment.

The apparatus of the present invention further includes guide means for guiding the carrier strips and elastic ribbons along predetermined paths. This is necessary to suit the generally hourglass or other outline of a stretched form fitting disposable diaper with cut out portions in the leg areas. The guide means directs the carrier strips and attached elastic ribbons to follow an hourglass outline or other contemplated pattern, thus ensuring that the carrier strip and elastic ribbons track the predetermined path on the longitudinal diaper margins which may be linear or curvilinear. The present invention further includes an elasticized leg disposable diaper that have the drawable carrier strips in its construction. The strips are incorporated along with the absorbent pad, backing sheet, and facing sheet in the diaper. Being readily flexible and of light weight, the carrier strips add neither bulk nor weight to the diaper and they do not affect the diaper performance in any way.

Other objects and advantages of the invention will become apparent from the disclosure.

DETAILED DESCRIPTION OF THE INVENTION

Although the disclosure hereof is detailed and exact to enable those skilled in the art to practice the invention, the physical embodiments herein disclosed merely exemplify the invention which may be embodied in other specific structure. The scope of the invention is defined in the claims appended hereto.

Figures 1, 5:
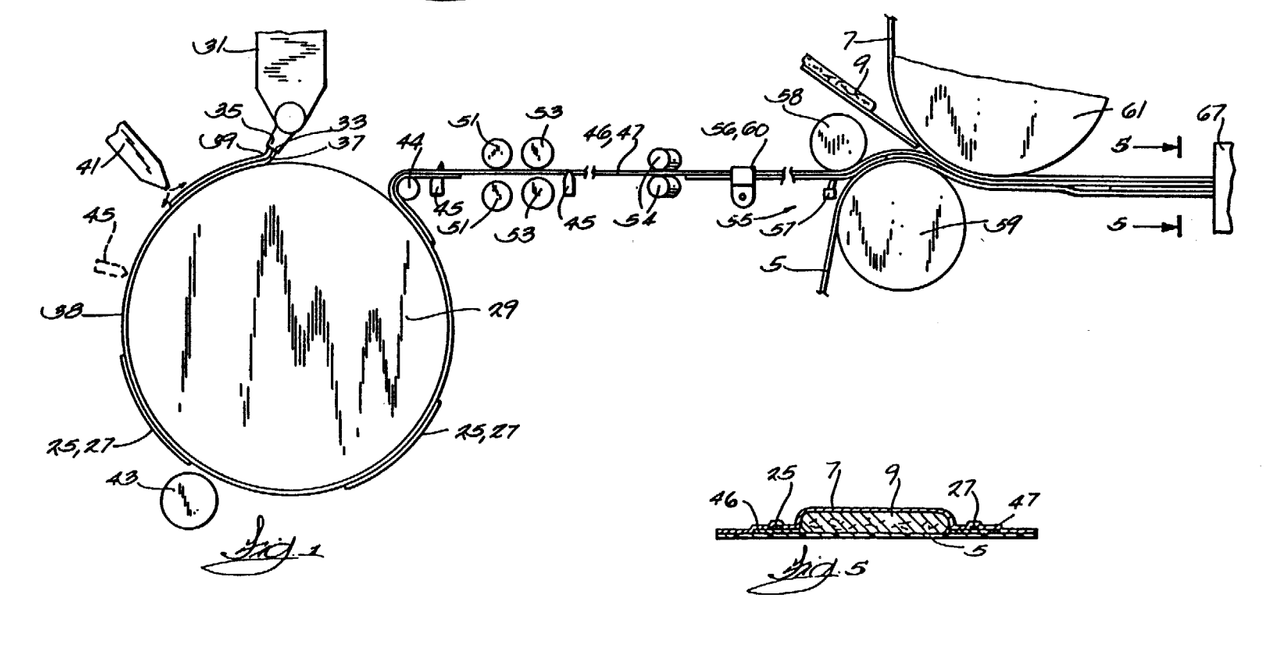
FIG. 1 is a schematic side view of the manufacturing apparatus of the present invention.
FIG. 5 is a cross-sectional view taken along lines 5—5 of FIG. 1.
Figure 2:
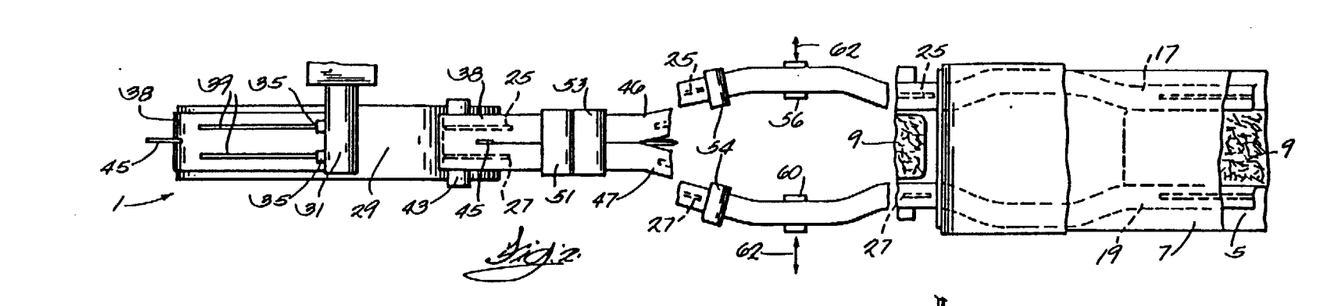
FIG. 2 is a schematic top view, partially broken, of the apparatus of the present invention.

Referring to FIGS. 1 and 2, manufacturing apparatus 1 is illustrated which includes the present invention. The apparatus finds particular usefulness for manufacturing elastic leg disposable diapers such as is illustrated at 3 in FIG. 3 and is disclosed in U.S. Pat. No. 4,410,324 incorporated herein by reference. However, it will be understood that the invention is not limited to producing products for incontinent applications.

Figures 3, 4:
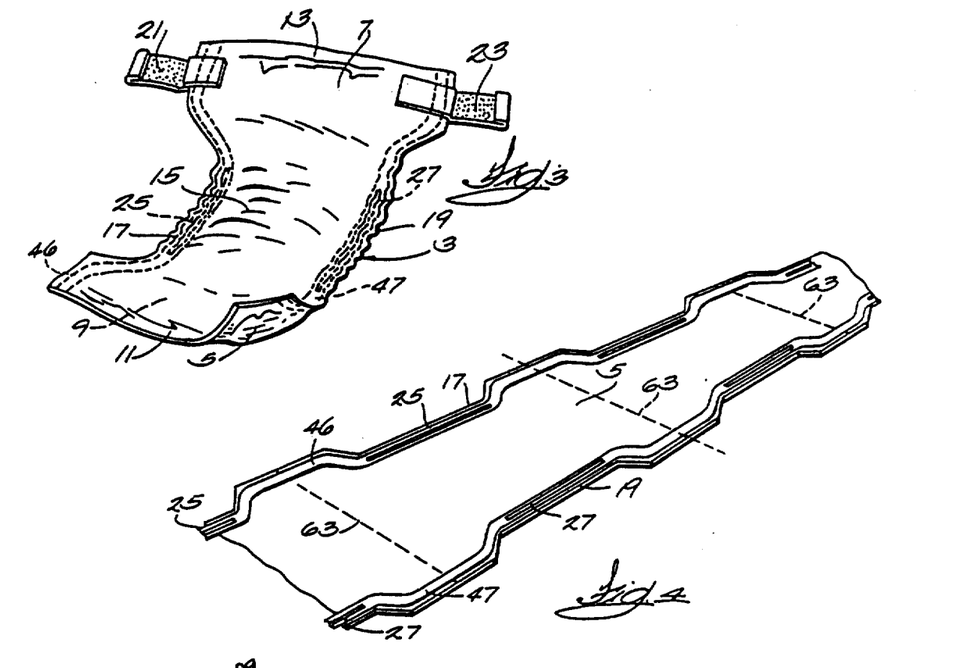
FIG. 3 is a perspective view of a finished elasticized leg disposable diaper manufactured by the method and apparatus of the present invention.
FIG. 4 is a perspective view of a diaper sheet in the extended flat condition, which occurs only during the diaper manufacturing process and which is manufactured by the method and apparatus of the present invention.

Referring to FIG. 3, the disposable diaper 3 has a backing sheet 5, a facing sheet 7, and absorbent pad 9 interposed between the backing and facing sheets, a front waist area 11, a rear waist area 13, and a crotch area 15 intermediate the two waist areas. Leg areas 17 and 19 are located laterally of the crotch area and intermediate the waist areas. Preferably, the leg areas are indented with respect to the waist areas, so that the stretched diaper has a generally hourglass contour. Waist fastening tapes 21 and 23 may be bonded to the corners of the rear waist area, and they are fastenable to the front waist area when the diaper is fitted to a wearer.

In accordance with the present invention, the manufacturing apparatus 1 (FIGS. 1 and 2) permit the diaper 3 to utilize a pair of transversely spaced elastic ribbons 25 and 27 in an economical and convenient manner. FIG. 1 shows the formation of one elastic ribbon of the pair. The elastic ribbons 25 and 27 are attached to the margins of the diaper in the leg areas 17 and 19, (FIGS. 3, 4) respectively, to elasticize the leg areas and thus provide a snug fit around the legs of the wearer. In FIG. 3, the elastic ribbons 25 and 27 are shown in a relaxed condition in which they cause random pleating or puckering of the back sheet 5, facing sheet 7, and absorbent pad 9.

Figure 7:
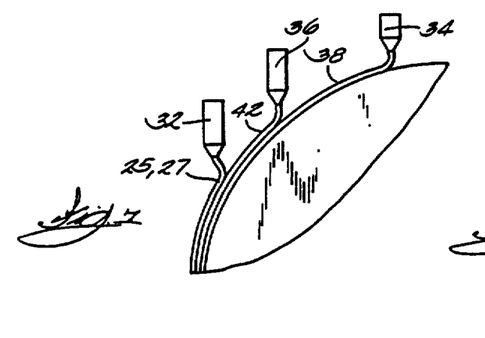
FIG. 7 is a diagrammatic view showing extrusion of a carrier strip, adhesive and elastic.

The manufacturing apparatus in FIG. 1 for supplying the elastic ribbons 25 and 27, FIGS. 1 and 2, includes a chill roll 29 of relatively large diameter and relatively short length. Alternatively, a chilled carrier belt can be employed. For example, the chill roll may be approximately 23 inches in diameter and about 4 inches long. An extruder head 31 having a lower nozzle 33 and a pair of upper nozzles 35 is located above the top point of the chill roll. Alternatively, the extruded carrier strips can be deposited on a flat moving carrier as subsequently described. The extruder head is capable of co-extruding two different materials simultaneously. Alternatively, nozzles 33 and 35 may be contained within separate but adjacent extruder heads 32, 34, as illustrated in FIG. 7.

In the illustrated construction in FIG. 1, the lower nozzle 33 extrudes a thin continuous stream of material 37 across the periphery of the chill roll. The material is preferably drawable when cooled, and the preferable drawable material is polypropylene. The carrier strips are cooled below the polymer softening point. Thus, upon cooling, the stream of material 37 is transformed into a thin and flexible carrier strip 38. Upper nozzles 35 of extruder head 31 extrude pairs of transversely spaced streams 39 of material that are superimposed upon and adhere to the stream 37 of drawable material. The extruder head 31 includes conventional valves operating under a control system, not illustrated, for controlling nozzle 35. The control system operates in well known fashion to open and close the valves so that the streams 39 from nozzle 35 are extruded intermittently onto the continuous film stream 37. The lengths of the streams 39 are related to the length of the diaper leg areas 17 and 19 (FIGS. 3, 4) as will be explained presently. The elastic ribbons may be extruded with a variable cross section by the use of conventional valves in conjunction with a control system as disclosed in pending application Ser. No. 530,544 to provide greater tensions in the crotch area than in the waistband region. If adhesives are to be used a third extrusion nozzle 36 is added to extruder head 31.

Figure 6:
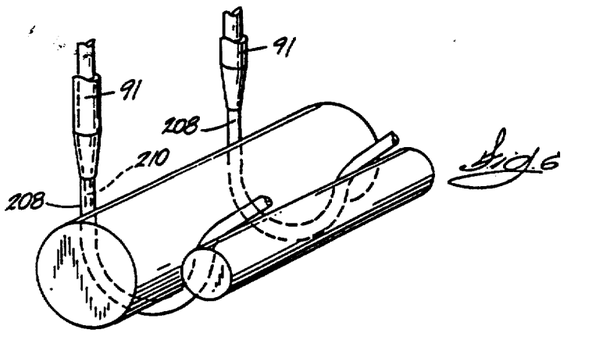
FIG. 6 is a diagrammatic view showing co-extrusion of two carrier tubes with internal elastic ribbons.
Figure 8:
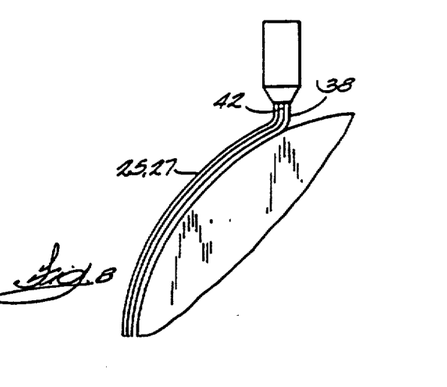
FIG. 8 is a diagrammatic view of co-extrusion of a carrier, adhesive and elastic.
Figure 18:
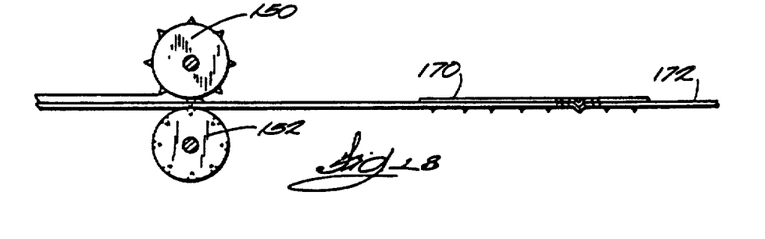
FIG. 18 is a side view of the diagram shown in FIG. 17.

The streams 37 and 39 can be cooled initially by using ambient air or by air from air jets 41. Additional cooling may be provided by one or more secondary chill rolls 43 that contact the streams 39 to flatten and cool them. The streams 39, after cooling and solidifying, acquire elastomeric properties, thereby creating pairs of elastic ribbons 25 and 27 that are firmly bonded to the underlying carrier strip 38. The roller 43 and/or the surface of the drum 29 can be patterned or corrugated to provide an interlocking pattern to secure the elastic to the, carrier strip as illustrated in FIG. 18. In FIG. 7 and 8 a band of adhesive 42 is extruded unto the carrier strip 38 prior to deposition of the elastic 25, 27. Similarly in FIG. 6 the same procedure is accomplished with a co-extrusion nozzle. The carrier strip can be extruded as a tube 208 with the elastic 210 extruded within the tube by co-extrusion nozzles 91. Alternatively the elastic ribbon can be extruded as a tube enclosing the carrier member filament which can be extruded or fed from a parent roll shown in FIG. 21 and FIG. 22 and FIG. 23. The filament can be of the same material as a carrier strip and hence is drawable. Securing the elastic to the carrier strip by adhering, bonding, securing, self-adhering, or mechanical bonding are within the purview of the invention and all mean the securement of the elastic to the carrier strip.

The cooled carrier strip 38 with elastic ribbons 25 and 27 bonded thereto pass around roller 44. The carrier strip is then slit longitudinally at about its transverse midpoint into two strips 46 and 47 by a stationary or rotary knife 45. Alternately the carrier may be slit with a hot knife on chill roll 29 or after draw rolls 53 with a stationary or rotary knife, or the carrier-elastic laminate may be slit immediately after deposition on the chill roll while in a heat softened condition with a hot knife as in FIG. 24. In the event carrier tubes are extruded as in FIG. 6, the knife 45 is not necessary. The carrier strips and elastic ribbons next pass between a pair of pull rolls 51 and a pair of draw rolls 53. The draw rolls 53 rotate at approximately 1⅛ to 3 times the speed of the pull rolls 51. Consequently, the carrier strips and elastic ribbons are stretched to approximately 1⅛ to 3 times their original lengths. The drawable properties of the carrier strips permit the stretching without detrimental effect. The stretching tension is maintained throughout the remainder of the manufacturing process The two carrier strips are separated transversely from each other, as shown in FIG. 2, by means of two pairs of drive rolls 54.

As shown in FIGS. 3 and 4, the leg areas 17 and 19 of the diaper are cut from the diaper sheet so that the stretched diaper acquires an hourglass contour. To permit the carrier strips to conform to the hourglass contour, the carrier strips 46 and 47 pass between a pair of transversely reciprocating or oscillating guides 56 and 60, respectively. Reciprocating, as used herein, includes oscillating or any form of curvilinear or straight line motions. The guides reciprocate in opposite directions, as indicated by arrows 62. They may be actuated by any suitable mechanism, as, for example, a cam and follower arrangement not illustrated in FIGS. 1 and 2. Consequently, the elastic ribbons are attached near the contoured margins of the finished diaper. The reciprocation of guides 56 and 60 is in timed relationship to the feeding of the absorbent pads 9 at diaper assembly station 55 so that the absorbent pads are located transversely and longitudinally symmetrical with respect to the hourglass contours of elastic ribbons 25 and 27. It will be noted that the length of stretched elastic ribbons approximate the longitudinal length of the leg areas. Thus, the length of the streams of material 39 extruded onto chill roll 39 may be less than the length of the diaper.

At the assembly station 55, the backing sheet 5, which is fed from a parent roll not illustrated in FIGS. 1 and 2, is bonded to the properly guided carrier strips 46 and 47 by adhesive applied to the carrier strips from a pair of applicators 57 located directly under a backing roll 58, FIG. 1. The tension in the carrier strips and elastic ribbons cause the backing sheet to adhere to the carrier strip as the backing sheet and carrier strips pass over roll 59. Subsequently, the absorbent pad 9 and facing sheet 7, which are applied in a conventional fashion from supply stations not shown, are fed to the nip between rollers 59 and 61 where they are bonded in a well known manner to form a continuous web of connected diapers. After the diaper components are assembled, as shown in FIG. 5, the continuously moving web is transported to a first cutting station 67 where the leg areas 17 and 19 are cut from the web as illustrated in U.S. Pat. No. 4,410,324. The web then passes to a second cutting station where it is transversely severed, as along lines 63, FIG. 4. At that time the tension of the elastic ribbons is relaxed, and the individual diapers assume the puckered shape of FIG. 3.

Figure 9:
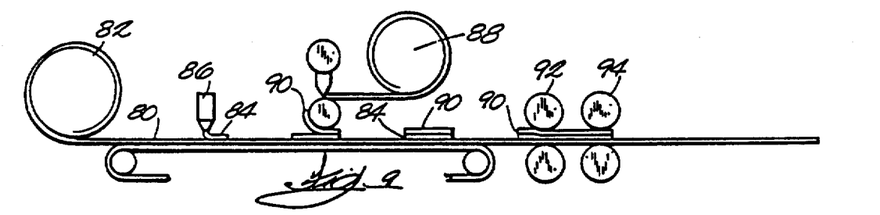
FIG. 9 is a diagrammatic view of a modified embodiment in which the carrier strip and elastic are supplied from parent rolls of ribbon.

FIG. 9 shows an alternate embodiment of the apparatus and method in which the carrier strip 80 is supplied from a parent roll 82. Adhesive 84 is supplied to the carrier strip 80 by an applicator 86. Elastic ribbon is supplied from a roll 88 and cut into discrete lengths 90. Feed and draw rollers 92, 94 stretch the film 80 and elastic 90.

Figure 10:
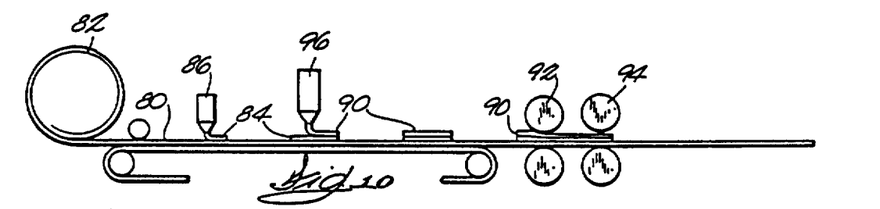
FIG. 10 is a diagrammatic view of a modified embodiment in which the adhesive and elastic are extruded.

FIG. 10 shows a modified embodiment in which the elastic ribbon is extruded by an extruder 96.

Figure 11:
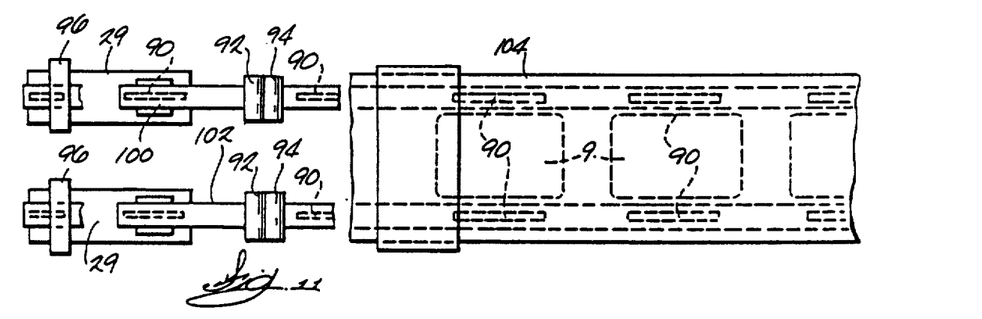
FIG. 11 is a plan view similar to FIG. 2 showing linear application of carrier tubes and elastic ribbon in a linear pattern.

FIG. 11 is a view similar to FIG. 10 showing two separate carrier strips 100, 102 which can be extruded or taken from two spaced parent rolls 82. The elastic 90 can be supplied by extruders as illustrated in FIG. 10. Draw roller sets 92, 94 draw the elastic carrier strips and stretch the elastic strips 90. The carrier strips 100, 102 are applied to a backing or facing sheet 104 spaced to accomodate deposition of pads 9 which are covered with a top sheet.

Figure 12:
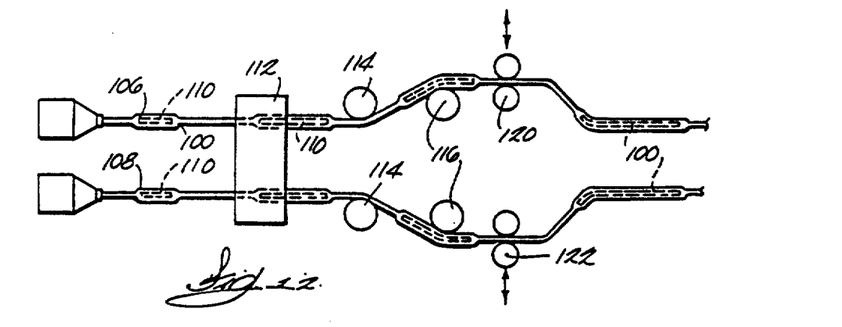
FIG. 12 is a plan view showing application of carrier tubes and elastic in an hour glass pattern.

FIG. 12 is a plan view showing coextrusion of carrier tubes 106 and 108 of drawable material with elastic cores 110 carried within the tubes. The elastic is intermittently extruded. The composite spaced carrier tubes and elastic are drawn and elastic stretched by pairs of draw rollers at station 112. The drawn tubes are guided by guide rollers 114, 116 and can be deposited on a facing or backing sheet by reciprocating rollers 120, 122 which reciprocate in a transverse direction. Chill rolls can also be employed between the extruders and draw rollers in FIGS. 11 and 12. The chill rolls do not contact the elastic when contained within a carrier tube.

Figure 13:
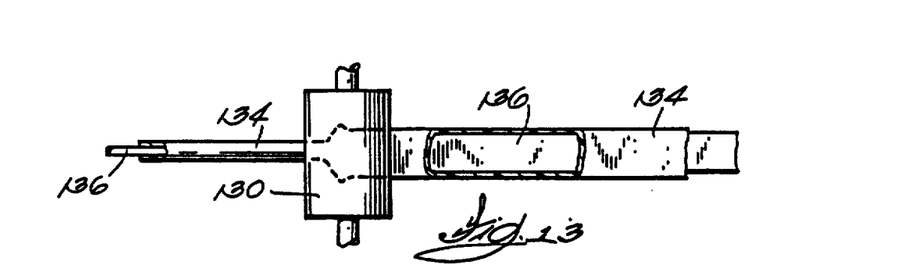
FIG. 13 is a diagrammatic plan view of a carrier strip in the form of a tube with the elastic ribbon inside the tube.
Figure 14:
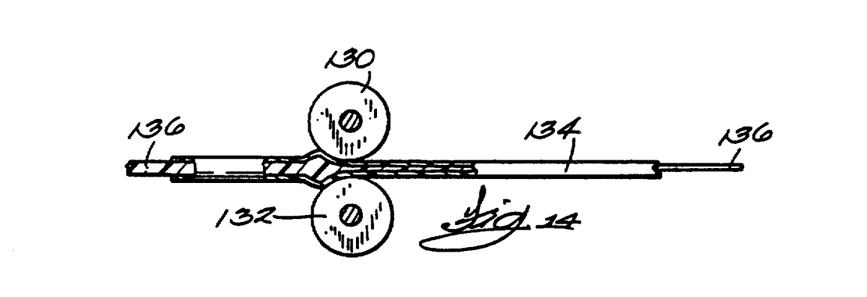
FIG. 14 is a side view of the diagram in FIG. 13.

FIGS. 13 and 14 show application of chill rollers 130, 132 to an extruded carrier tube 134 containing a continuous elastic core 136.

The chill rollers flatten or form the tube into a band strip, or narrow web.

Figure 15:
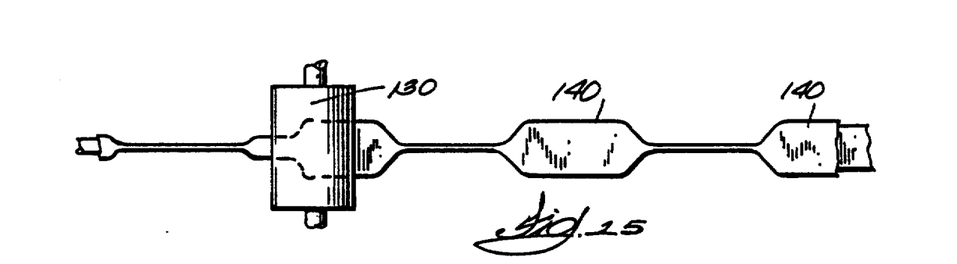
FIG. 15 is a diagrammatic plan view of a carrier strip in the form of a tube with elastic intermittently extruded.
Figure 16:
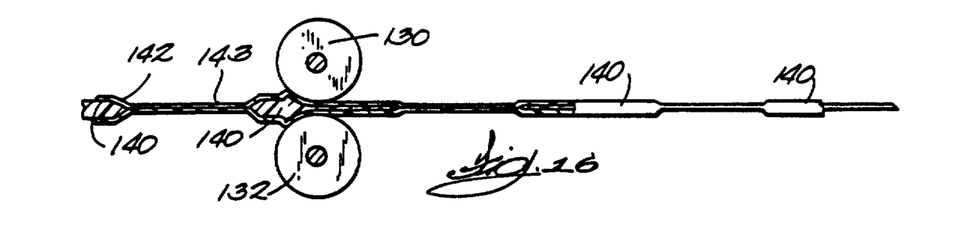
FIG. 16 is a side view of the diagram in FIG. 15.

FIGS. 15 and 16 show the application of chill rolls 130, 132 to an extruded elastic-carrier strip assembly in which the discrete lengths of elastic 140 are intermittently extruded within the carrier tube 142. The elastic lengths are connected by small carrier tube lengths 143. Upon flattening, the carrier strip will have the appearance shown in FIG. 15.

Figure 17:
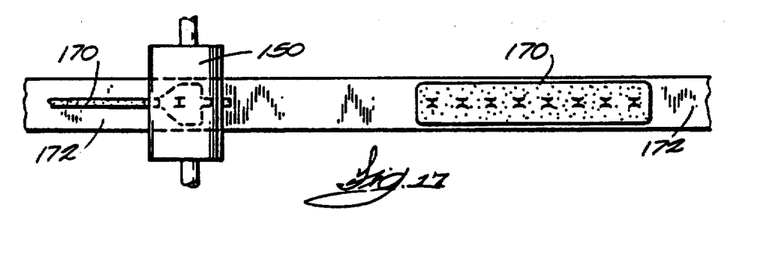
FIG. 17 is a plan view of a pattern rolled carrier tube with internal elastic ribbon.

FIGS. 17 and 18 show the use of patterned chill rolls 150 and 152 which mate to form an interlocking pattern of the squeezed and formed elastic ribbon 170 on a carrier strip 172. Adhesive could also be employed to secure the elastic to the carrier strip.

Figure 19:
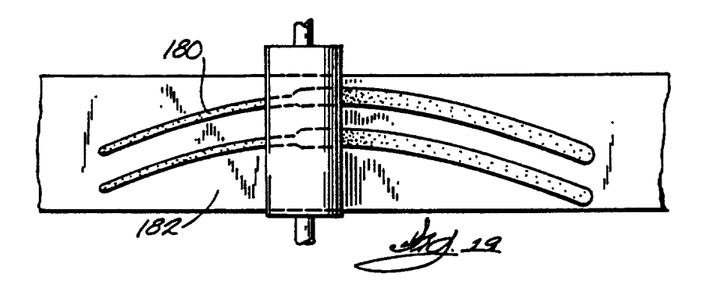
FIG. 19 is a plan view of elastic ribbon deposited in non-linear pattern on a carrier strip and squeeze roller.
Figure 20:
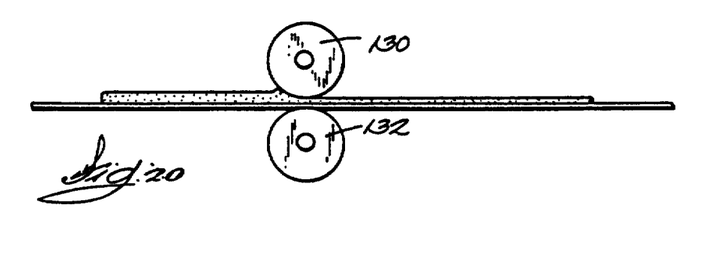
FIG. 20 is a side view of the diagram in FIG. 19.

FIGS. 19 and 20 show intermittent deposition of discrete elastic lengths 180 in a pattern on a flat carrier strip 182. The patterned deposition of the elastic can be provided by reciprocating the extruders.

FIG. 23 shows a drum 200 with corrugating teeth 202 which cooperate with corrugating roll 204 to corrugate the backing or facing sheet 206. An assembly of a filament 208 within an elastic tube 210 or spaced tube segments 210 is applied over the corrugated backing. FIGS. 21 and 22 show the filament 208 and tube 210.

The filament 208 can be extruded from an extruder 212 or alternatively supplied from a parent roll 214. The filament is fed through the nozzle of the extruder and the elastic extruded around it.

Draw rolls 220 pull the assembly or lamina from the roll 200 and simultaneously remove the corrugations, draw the carrier filament 208 and stretch the elastic tube 210. The lamina is then assembled with a pad 224 and the other of a backing or facing sheet 226 while the elastic remains stretched.

Thus, it is apparent that there has been provided, in accordance with the invention, methods and apparatus for economically and conveniently forming and transporting individual pieces of elastic ribbon that fully satisfy the objects, aims, and advantages set forth above. While the invention has been described with specific embodiments thereof, it is evident that many alternatives, modifications, and variations will be apparent to those skilled in the art in light of the foregoing description. Accordingly, it is intended to embrace all such alternatives, modifications, and variations as fall within the spirit and broad scope of the appended claims.

The carrier strip and elastic ribbons can be firmly adhered by autogenous bonding if the materials are compatible. If the carrier strip and elastic ribbon are dissimilar materials and not compatible with each other, an adhesive is used for securement. A mechanical bond or a mechanical interlock can be used solely by itself or in conjuction with self bonding, autogenous bonding, or adhesive bonding. The term autogenously bonded as used herein is used to describe the tendency of the two layers to adhere to each other when the surfaces are brought into contact with or without heat or by the application of heat and pressure alone and without any solvent or adhesive application. The terms self adhering, self bonding, autogenous bonding and mechanical bonding (obtained by passing heat softened extrudates between two patterned chill rolls) as used herein are used interchangeably and means the attachment or the securement without the use of solvents or adhesives. The terms secure, attach, bond and adhere as used herein means attachment or securement by any one or any combination of above listed terms and including the use of adhesives and solvents. The term adhesive bonds as used herein means the attachment or bonding with the use of materials having adhesive properties or solvents.

Thermoplastic rubbers suitable for extrusion such as Shell Chemical Company's Kraton 2000 and 3000 Series and GX-2701, DuPont's thermoplastic elastomer, Alcryn, B. F. Goodrich's thermoplastic polyurethanes, Upjohn's thermoplastic polyurethanes, J. Von's thermoplastic elastomers, Stevens thermoplastic film and Mearthane Products polyurethane elastomers are thermoplastic rubbers which can be employed for the elastic bands. These rubbers combine the properties of vulcanized elastomers and the processing of vulcanized elastomers and the processing advantages of thermoplastics. Standard thermoplastic processing equipment can be used to form the rubber processing equipment can be used to form the rubber extrudates. The present invention, however, is not limited to the above listed thermoplastic rubbers, for any elastic thermoplastic material which is soft and flexible will be suitable for the aforementioned elastic bands.

Both natural and synthetic vulcanized rubbers can be secured to the extruded carrier strip and fed into the stretch and draw unit and subsequently to the assembly station, or the carrier strip, as used, may be in a roll form, or the carrier strip and the elastic ribbon may be assembled as a laminate in roll form prior to being unwound into the assembly station.

Although the above mentioned thermoplastic rubbers can be processed in ways similar to those used for conventional thermoplastic polymers, it is very difficult to extrude them into thin films. However, by extruding a thick film of thermoplastic rubber onto a carrier strip and squeezing said molten or fused extrudate between two chill rolls, thin films of any desirable thicknesses are obtained, and can range from less than 0.0001" to 1/16" or more. By using chill rolls with patterns, as herein disclosed, cross-sectional shapes and forms in varying thicknesses can be fabricated in various forms such as tapered, bell shaped or double ribbons connected by a thin web some of which are shown in the drawings.

In the preferred method, the carrier strip is prepared by extruding molten or fused polymer through a slotted or tubular orifice and drawing the polymer away from the orifice at a velocity greater than the velocity of extrusion to effect a substantial draw-down in the molten state prior to solidification, thereby achieving at least partial molecular orientation of long chain molecules as well as a great reduction in cross-sectional area during the hot draw-down while being cooled by the ambient air. The extent to which the molecular orientation is achieved depends on the amount the carrier strip is stretched, which is controlled by the speed with which the polymer is ejected from the die, the speed of withdrawal, and the degree of cooling by the ambient air. To further speed up cooling and setting of the partially drawn carrier strip, secondary air, fluid, or vapor streams may be introduced prior to contact with the chill roll, whereupon the partially hot drawn carrier strip is cooled to a set condition. Alternatively, sufficient chilling of the secondary fluid streams will cool the carrier strip to a set condition without the necessity or need of a chill roll.

Subsequent to the final cooling by the secondary fluid means or by the chill roll means adhesive and fused elastic material are deposited on the cooled carrier strip, which is in direct contact with the chill roll, whereon the elastic strip solidifies to a set condition and becomes elastomeric or stretchable and bonded to the carrier sheet. Following solidification of the elastic ribbon, the two materials are subjected to a cold stretch wherein drawing takes place at a temperature below the polymer melting point, and the elastic ribbon is stretched. This draw is continued until the desired additional amount of molecular orientation has been imparted to the carrier strip. If a coextrusion die is used the coextruded laminate of carrier sheet, adhesive, and elastic ribbon are cooled simultaneously and subsequently drawn as described above. The total amount of orientation imparted to the carrier strip is determined by the following three requirements.

1. The final thickness of the carrier strip as it enters the assembly station with very thin materials being highly cost efficient. The material thickness may range from 0.0001" to 0.015" preferably 0.00015" to 0.0008."

2. The amount of elongation to be imparted to the elastic by the wearer of the garment, the range being from 10% to 600% elongation to preferably 20% to 300%.

3. The remaining amount of stretch or drawing to be left in the carrier strip to allow efficient machine operation without strip breakage and costly shutdowns. If the polymer used is of sufficient strength the strip may be substantially fully drawn which greatly reduces material costs.

In addition to self bonding, autogenous bonding, and fuse bonding, the elastic ribbons may be secured with adhesives some of which are listed below. They may be applied with applicators, both hot and cold; extruded, and co-extruded whereby they are extruded with one or both of the materials to be bonded to each other. Suitable adhesives are pressure sensitive adhesives, cold adhesives, hot melt adhesives, releasable adhesives, elastomeric hot melt adhesives, and pressure sensitive hot melts. Some of the manufacturers supplying suitable adhesive are as follows: Eastman Chemical Co., Hot Melt Adhesive No. 13375; H. B. Fuller Co., Hot Melt Adhesive No. HM1533; Shell Chemical Co., Kraton; Rohm and Haas Co., Hot Melt Adhesive QR-969; Borden Chemical Co., Casco Melt HA-7981, and Findley Co., Elastomeric Hot Melt Adhesives.

Suitable thermoplastic polymers suitable for use in the instant invention include the following: Polyolefins-polyethylenes, polypropylenes; polyamides-nylons; polyesters; polyurethanes; polyacrylics; polyvinyl acetate; including copolymers of such compounds and mixed polymers of such compounds. Any drawable thermoplastic polymer or at least partially drawable polymer can be used for the carrier strip even though it contains some elastomeric material. As used herein the term "carrier strip" and "carrier member" are used interchangably and both include filaments.

I claim:

1. Apparatus for continuously forming and transporting elastic ribbons comprising:
   (a) support means;
   (b) first extrusion means for extruding a continuous stream of drawable first material for a carrier strip onto the support means, the first material being drawable when cooled below its polymer softening point;
   (c) second extrusion means including control means for extruding at least one intermittent stream of a second material onto the undrawn stream of first material, the second material having elastomeric properties when cooled and being non-elasticized when received by said first material;
   (d) cooling means for cooling the extruded streams of first and second material, thereby transforming the first material into a flexible carrier strip of drawable material and the second material into an elastic ribbon bonded to the carrier strip;
   (e) means for moving the carrier strip and elastic ribbon from the support means;
   (f) means for drawing said carrier strip to elongate said carrier strip while simultaneously stretching said elastic ribbon bonded thereto;
   (g) means for combining said drawn and stretched material while stretched with a pad and a web; and
   (h) means for cutting discrete units from the combined web and carrier strip with said elastic ribbon having a relaxed length less than the web.

2. The apparatus of claim 1 wherein the support means is a chill roll, and wherein at least one secondary chill roll presses and cools the stream of second material.

3. The apparatus of claim 1 wherein the cooling means includes at least one jet for supplying cooling medium to the first and second extruded materials immediately after extrusion.

4. The apparatus of claim 1 wherein the first material is polypropylene.

5. In combination with equipment for manufacturing elastic leg disposable diapers including an assembly station for continuously assembling the diapers from a backing sheet, a facing sheet, and absorbent pads, apparatus for continuously supplying discrete lengths of elastic ribbon without waste to the assembly station for elasticizing the diaper legs by applying the elastic ribbon along the longitudinal margins of the diapers comprising:
   (a) support means;
   (b) first extrusion means for continuously extruding a thin stream of first material onto the periphery of the support means, the first material being cold drawable when cooled;
   (c) second extrusion means including control means for extruding pairs of transversely space intermittent streams of a second material onto the stream of first extruded material, the second material having elastomeric properties when cooled and being self-adhering to the first extruded material;
   (d) cooling means for cooling the first and second streams of material to produce the cold drawable and elastomeric properties of the first and second extruded materials, respectively, thereby creating a carrier strip with pairs of elastic ribbon adhered thereto;

(e) knife means for slitting the carrier strip longitudinally intermediate the pairs of elastic ribbons to form two carrier strips with elastic ribbons adhered thereto, (f) stretch means for stretching the two carrier strips and elastic ribbons having adhered thereto a predetermined amount; and (g) means to transversely separate the slitted stretched carrier strips having said elastic ribbons adhered thereto and to feed the carrier strips and elastic ribbons to the assembly station and apply the elastic ribbon in a stretched condition to the diaper backing or facing sheet.

6. The combination of claim 5 wherein the cooling means includes at least one air jet for directing cooling air onto the extruded streams of first and second material and at least one secondary chill roll for forming and cooling the stream of second extruded material.

7. The combination of claim 5 further comprising:

(a) guide means for guiding the two carrier strips and elastic ribbons into the assembly station along predetermined paths that conform to the longitudinal margins of the diapers; and (b) applicator means for applying adhesive to the carrier strips to attach the carrier strips to the backing sheet and/or facing sheet, so that the elastic ribbons are attached near the longitudinal margins of the diaper.

8. The combination of claim 7 wherein the guide means comprises a pair of transversely reciprocable guides that reciprocate in opposite directions in timed relationship to the assembly of the absorbent pad to the backing and facing sheets to position the elastic ribbons in the leg areas of the diapers.

9. A method of continuously forming and transporting elastic ribbon to selected processing stations comprising the steps of:

(a) extruding a continuous thin stream of a first material onto the periphery of a roll rotating about an axis, the first material being at least partially drawable when cooled;

(b) intermittently extruding at least one stream of a second material onto the stream of first material, the second material having elastomeric properties when cooled and being self-adhering to the first material;

(c) cooling the first and second extruded materials to develop the cold drawable and elastomeric properties, respectively, of the first and second material, thereby producing a cold drawable carrier strip with the elastic ribbon bonded thereto; and (d) transporting the carrier strip and elastic ribbon to a processing station.

10. The method of claim 9 comprising the further step of stretching the carrier strip and elastic ribbon a predetermined amount subsequent to cooling the streams of first and second extruded materials.

11. The method of claim 9 wherein the stream of second material is extruded intermittently onto the stream of first material.

12. The method of claim 9 wherein at least two streams of second material are extruded in laterally spaced relationship onto the stream of first material thereby forming at least two elastic ribbons, and comprising the further step of:

slitting the carrier strip longitudinally intermediate the elastic ribbons.

13. The method of claim 12 comprising the additional step of:

separating the slit carrier strips transversely a predetermined amount.

14. The method of claim 13 comprising the additional steps of:

transversely guiding the carrier strips along predetermined paths to the selected processing station.

15. A method of continuously manufacturing an elastic leg disposable diaper having front and rear waist areas and a crotch area intermediate the two waist areas, the crotch area having leg areas positioned laterally thereof and intermediate the waist areas comprising the steps of:

(a) extruding a continuous thin stream of a first material onto the periphery of a rotatable roll, the first material being cold drawable when cooled;

(b) intermittently extruding pairs of laterally spaced streams of a second material onto the stream of the first material, the second material having elastomeric properties when cooled and being self-adhering to the first material;

(c) cooling the first and second extruded materials to develop the cold drawable and elastomeric properties, respectively, of the first and second materials, thereby producing a flexible carrier strip and pairs of elastic ribbons adhered thereto, respectively;

(d) slitting the carrier strips longitudinally into two carrier strips, each carrier strip having an intermittent elastic ribbon attached thereto;

(e) simultaneously stretching the carrier strips and elastic ribbons a predetermined amount;

(f) separating the two carrier strips transversely a predetermined amount;

(g) bonding the carrier strips to the outer margins of a diaper backing or facing sheet formed as a continuous web;

(h) assembling an absorbent pad and a continuous web facing sheet to the backing sheet, the absorbent pad being interposed between the backing sheet and facing sheet and being located in the diaper crotch area; and (i) transversely severing the backing sheet, facing sheet, and the carrier strips at predetermined intervals to create individual diapers, so that the stretched elastic ribbons relax to pucker the disposable diaper, at least in the crotch area.

16. The method of claim 15 wherein the step of cooling the extruded first and second materials includes the steps of:

(a) cooling the rotatable roll;

(b) blowing cooling air onto the extruded first and second materials; and (c) contacting the extruded second material with at least one secondary chill roll.

17. The method of claim 16 wherein the step of bonding the carrier strips to the backing sheet includes the step of locating the elastic ribbons in the leg areas of the diaper.

18. The method of claim 17 comprising the steps of:

(a) transversely guiding the carrier strips into relation with the backing sheet in a generally hourglass contour symmetrically straddling the absorbent pad prior to bonding the carrier strip to the backing and/or facing sheet; and (b) cutting the backing and facing sheets to conform to the hourglass contour of the carrier strips prior to transversely severing the backing and facing sheets and carrier strips,
so that the diaper leg areas conform to the legs of the wearer.

19. Apparatus for continuously forming and transporting elastic ribbons comprising:
    (a) support means;
    (b) first extrusion means for extruding a continuous stream of first material for a carrier strip onto the support means, the first material being at least partially drawable when cooled;
    (c) second extrusion means including control means for extruding at least one intermittent stream of a second material onto the stream of first material, the second material having elastomeric properties when cooled;
    (d) cooling means for cooling the extruded streams of first and second materials, thereby transforming the first material into a flexible carrier strip of drawable material and the second material into an elastic ribbon bonded to the carrier strip;
    (e) transport means for transporting the carrier strip and elastic ribbon from the support means;
    (f) means for drawing said carrier strip while simultaneously stretching said elastic ribbon bonded thereto; and
    (g) means for combining said drawn and stretched material with a pad and film assembly.

20. The method of making a diaper comprising the steps of providing a carrier strip, adhering an elastic ribbon to the carrier strip by intermittently extruding the elastic ribbon onto the carrier strip at spaced intervals, tensioning the adhered elastic ribbon and combining the carrier strip and diaper backing, facing sheets and absorbent pads to form a chain of diapers while the elastic ribbon is under tension, and cutting individual diapers from the chain.

21. The method of claim 20 wherein the carrier strip and elastic are co-extruded.

22. The method of claim 21 where the carrier strip is in the form of a tube with the elastic located therewithin.

23. The method of claim 22 including the step of adhering the elastic to the carrier strip with adhesive.

24. The method of making a diaper comprising the steps of providing a carrier strip, adhering an elastic ribbon to the carrier strip by intermittently extruding the elastic ribbon onto the carrier strip at spaced intervals, tensioning the adhered elastic ribbon and combining the carrier strip and diaper backing, facing sheets and absorbent pads to form a chain of diapers while the elastic ribbon is under tension, and cutting individual diapers from the chain, including the step of corrugating the carrier strip and elastic ribbon assembly prior to applying to the backing and facing sheets.

25. Apparatus for continuously forming and transporting elastic ribbons comprising:
    (a) web supply means for supplying one or more relatively narrow spaced webs of carrier strip;
    (b) elastic ribbon supply means including control means for intermittently supplying an elastic ribbon to each of said carrier strips;
    (c) means for securing said elastic ribbon to said carrier strip;
    (d) means for drawing said carrier strip and stretching said elastic ribbons; and
    (e) means for combining said drawn carrier strip and stretched ribbon while stretched with a pad and film web having a width greater than said carrier strips.

26. Apparatus for continuously forming and transporting elastic ribbons comprising:
    (a) first extrusion means for extruding a continuous stream of a first material for a carrier strip, the first material being drawable when cooled;
    (b) second extrusion including control means for extruding at least one intermittent stream of a second material onto the stream of first material, the second material having elastomeric properties when cooled, said
    (c) cooling means for cooling the extruded streams of first and second materials, thereby transforming said first material into a flexible carrier strip of drawable material and the second material into an elastic ribbon secured to the carrier strip;
    (d) means for drawing said carrier strip while simultaneously stretching said elastic ribbon secured thereto; and
    (e) means for combining said drawn and stretched material while stretched with a pad, backing and facing assembly.

27. Apparatus of claim 26 wherein first and second extrusion means is a coextrusion die.

28. Apparatus of claim 26 wherein coextrusion die emits a stream of a third material having adhesive properties.

29. Apparatus of claim 26 wherein the cooling means is a chill roll.

30. Apparatus of claim 29 wherein at least one secondary chill roll contacts and cools at least one stream of extrudate.

31. Apparatus of claim 30 wherein said secondary chill roll contains a pattern for shaping at least one stream of extrudate.

32. Apparatus of claim 29 wherein said chill roll is provided with a pattern for shaping at least one stream of extrudate.

33. Apparatus of claim 29 wherein the cooling means includes at least one jet for supplying cooling medium to extruded materials after extrusion.

34. Apparatus of claim 26 wherein the second extrusion means includes control means for imparting a preselected variable cross section to the streams of the second material.

35. The method of making a diaper comprising the steps of providing a carrier member for transporting elastic ribbons to the pad and facing assembly station, adhering an elastic ribbon to the carrier member, by intermittently extruding the elastic ribbon onto the carier strip providing a corrugated diaper backing or facing web, adhering carrier member elastic ribbon laminate to the corrugated backing or facing, simultaneously removing the corrugations and drawing the carrier member and stretching the elastic ribbon, and combining said web with absorbent pads and the facing or backing web to form a chain of diapers while the elastic ribbon is under tension, and cutting individual diapers from the chain.

36. The method of claim 35 wherein the carrier strip is fed from a parent roll.

37. The method of claim 35 wherein the elastic ribbon is composed of a self-adhering elastic composition.

38. The method of claim 35 where the elastic ribbon is in the form of a tube with the carrier strip therewithin.

39. The method of claim 35 including the step of adhering the carrier member elastic laminate to the backing or facing with adhesive.

40. The method of claim 21 wherein the carrier strip is in the form of a filament.

41. The method of claim 21 wherein the elastic ribbon is in the form of a tube with the carrier strip located therewithin.

42. The method of claim 37 including the step of adhering the elastic ribbon to the backing and facing.

* * * * *